United States Patent
Bandeira et al.

(10) Patent No.: US 8,303,601 B2
(45) Date of Patent: Nov. 6, 2012

(54) COLLET-ACTIVATED DISTRACTION WEDGE INSERTER

(75) Inventors: Carla Bandeira, Voorhees, NJ (US); David Talijan, Chestnut Ridge, NY (US)

(73) Assignee: Stryker Spine (FR)

( * ) Notice: Subject to any disclaimer, the term of this patent is extended or adjusted under 35 U.S.C. 154(b) by 883 days.

(21) Appl. No.: 11/448,416

(22) Filed: Jun. 7, 2006

(65) Prior Publication Data

US 2008/0071279 A1   Mar. 20, 2008

(51) Int. Cl.
 A61B 17/58 (2006.01)
 A61B 17/60 (2006.01)
 A61F 2/00 (2006.01)

(52) U.S. Cl. ............................ 606/99; 606/90
(58) Field of Classification Search .............. 606/99, 606/90, 104; 623/17.11–17.16
See application file for complete search history.

(56) References Cited

U.S. PATENT DOCUMENTS

| | | | |
|---|---|---|---|
| 5,831 A | 10/1848 | North | |
| 47,102 A | 4/1865 | Hartford | |
| 99,289 A | 2/1870 | Catlin et al. | |
| 319,095 A * | 6/1885 | Joel ........................... | 81/7 |
| 583,158 A | 5/1897 | Upham | |
| 1,584,464 A | 5/1926 | Maranville | |
| 2,243,717 A | 5/1941 | Moreira | |
| 2,472,103 A | 6/1949 | Giesen | |
| 3,574,381 A | 4/1971 | Ocheltree et al. | |
| 3,604,487 A | 9/1971 | Gilbert | |
| 3,867,728 A | 2/1975 | Stubstad et al. | |
| 3,867,932 A | 2/1975 | Huene | |
| 4,124,026 A | 11/1978 | Berner et al. | |
| 4,263,903 A | 4/1981 | Griggs | |
| 4,399,813 A | 8/1983 | Barber | |
| 4,455,898 A | 6/1984 | Marbourg, Jr. | |
| 4,526,072 A | 7/1985 | Manhoff, Jr. | |
| 4,716,894 A | 1/1988 | Lazzeri et al. | |
| 4,919,679 A | 4/1990 | Averill et al. | |

(Continued)

FOREIGN PATENT DOCUMENTS

EP    599419    6/1994

(Continued)

OTHER PUBLICATIONS

AlloCraftPL, Posterior Lumbar System, Product Information, Stryker Howmedica Osteonics, 2003.

(Continued)

*Primary Examiner* — Kevin T Truong
*Assistant Examiner* — David Bates
(74) *Attorney, Agent, or Firm* — Lerner, David, Littenberg, Krumholz & Mentlik, LLP

(57) ABSTRACT

A distraction wedge inserting and removing device, the device having an outer member with a handle and a shaft extending therefrom, the shaft having at least one collet formed between a pair of slots extending from a distal end of the shaft toward the handle, the at least one collet having a cammed surface on the interior surface thereof. The device also having an inner member with a roller and a rod extending therefrom from a proximal end of the inner member to a head at a distal end of the inner member, the rod being configured to interact with the handle to advance the rod within the outer member toward the distal end of the outer member, whereby the head interferes with the cammed surface of the at least one collet to move the at least one collet outwardly in a radial direction to secure a distraction wedge.

20 Claims, 4 Drawing Sheets

U.S. PATENT DOCUMENTS

| | | |
|---|---|---|
| 4,946,458 A | 8/1990 | Harms et al. |
| 4,950,270 A | 8/1990 | Bowman et al. |
| 4,994,064 A | 2/1991 | Aboczky |
| 5,029,498 A | 7/1991 | Kinsey |
| 5,029,598 A | 7/1991 | Stroszynski et al. |
| 5,116,339 A | 5/1992 | Glock |
| 5,123,926 A | 6/1992 | Pisharodi |
| 5,167,476 A * | 12/1992 | Lafferty et al. ............... 408/240 |
| 5,171,313 A | 12/1992 | Salyer |
| 5,176,683 A | 1/1993 | Kimsey et al. |
| 5,192,327 A | 3/1993 | Brantigan |
| 5,236,460 A | 8/1993 | Barber |
| 5,242,443 A | 9/1993 | Kambin |
| 5,306,308 A | 4/1994 | Gross et al. |
| 5,352,231 A | 10/1994 | Brumfield et al. |
| 5,370,697 A | 12/1994 | Baumgartner et al. |
| 5,423,825 A | 6/1995 | Levine |
| 5,429,641 A | 7/1995 | Gotfried et al. |
| 5,431,658 A | 7/1995 | Moskovich |
| 5,462,552 A | 10/1995 | Kiester |
| 5,484,132 A * | 1/1996 | George et al. ............... 248/231.9 |
| 5,490,859 A | 2/1996 | Mische et al. |
| 5,527,326 A | 6/1996 | Hermann et al. |
| 5,571,109 A | 11/1996 | Bertagnoli et al. |
| 5,605,080 A | 2/1997 | Pfefferle et al. |
| 5,607,424 A | 3/1997 | Tropiano et al. |
| 5,609,635 A | 3/1997 | Michelson |
| 5,628,751 A * | 5/1997 | Sander et al. ................. 606/104 |
| 5,649,931 A | 7/1997 | Bryant et al. |
| 5,653,762 A | 8/1997 | Pisharodi |
| 5,658,337 A | 8/1997 | Kohrs et al. |
| 5,683,399 A * | 11/1997 | Jones ............................. 606/91 |
| 5,713,903 A * | 2/1998 | Sander et al. ................. 606/326 |
| 5,720,751 A | 2/1998 | Jackson |
| 5,720,753 A | 2/1998 | Sander et al. |
| 5,732,992 A | 3/1998 | Mauldin |
| 5,741,253 A | 4/1998 | Michelson |
| 5,776,199 A | 7/1998 | Michelson |
| 5,782,830 A | 7/1998 | Farris |
| 5,782,919 A | 7/1998 | Zdeblick et al. |
| 5,860,973 A | 1/1999 | Michelson |
| 5,885,299 A | 3/1999 | Winslow et al. |
| 5,888,224 A | 3/1999 | Beckers et al. |
| 5,888,227 A | 3/1999 | Cottle et al. |
| 5,888,228 A | 3/1999 | Knothe et al. |
| 5,928,230 A | 7/1999 | Tosic |
| 5,989,289 A | 11/1999 | Coates et al. |
| 6,004,326 A | 12/1999 | Castro et al. |
| 6,017,305 A | 1/2000 | Bonutti |
| 6,080,193 A | 6/2000 | Hochshuler et al. |
| 6,083,225 A | 7/2000 | Winslow et al. |
| 6,110,179 A | 8/2000 | Flivik et al. |
| 6,113,602 A | 9/2000 | Sand |
| 6,113,605 A | 9/2000 | Storer et al. |
| 6,113,638 A | 9/2000 | Williams et al. |
| RE37,005 E | 12/2000 | Michelson et al. |
| 6,156,040 A | 12/2000 | Yonemura et al. |
| 6,159,215 A | 12/2000 | Urbahns et al. |
| 6,174,311 B1 | 1/2001 | Branch et al. |
| 6,179,875 B1 | 1/2001 | Von Strempel et al. |
| 6,189,422 B1 | 2/2001 | Stihl et al. |
| 6,193,721 B1 | 2/2001 | Michelson |
| 6,197,033 B1 | 3/2001 | Haid, Jr. et al. |
| 6,200,322 B1 | 3/2001 | Branch et al. |
| 6,245,108 B1 | 6/2001 | Biscup |
| 6,261,296 B1 | 7/2001 | Aebi et al. |
| 6,267,763 B1 | 7/2001 | Castro |
| 6,290,724 B1 | 9/2001 | Marino |
| 6,319,254 B1 | 11/2001 | Giet et al. |
| 6,319,257 B1 | 11/2001 | Carignan et al. |
| 6,328,746 B1 | 12/2001 | Gambale |
| 6,331,179 B1 | 12/2001 | Freid et al. |
| 6,342,057 B1 | 1/2002 | Brace et al. |
| 6,402,757 B1 | 6/2002 | Moore, III et al. |
| 6,436,117 B1 | 8/2002 | Waller et al. |
| 6,440,133 B1 | 8/2002 | Beale et al. |
| 6,440,136 B1 | 8/2002 | Gambale et al. |
| 6,440,142 B1 | 8/2002 | Ralph et al. |
| 6,454,807 B1 * | 9/2002 | Jackson ..................... 623/17.15 |
| 6,458,159 B1 | 10/2002 | Thalgott |
| 6,478,801 B1 | 11/2002 | Ralph et al. |
| 6,511,484 B2 | 1/2003 | Torode et al. |
| 6,524,312 B2 | 2/2003 | Landry et al. |
| 6,527,780 B1 | 3/2003 | Wallace et al. |
| 6,562,041 B1 | 5/2003 | Yonemura et al. |
| 6,565,573 B1 | 5/2003 | Ferrante et al. |
| 6,565,574 B2 | 5/2003 | Michelson |
| 6,569,168 B2 | 5/2003 | Lin |
| 6,589,247 B2 | 7/2003 | McGahan et al. |
| 6,599,294 B2 | 7/2003 | Fuss et al. |
| 6,599,320 B1 * | 7/2003 | Kuslich et al. ............. 623/17.11 |
| 6,613,091 B1 | 9/2003 | Zdeblick et al. |
| 6,626,347 B2 | 9/2003 | Ng |
| 6,648,888 B1 | 11/2003 | Shluzas |
| 6,648,895 B2 | 11/2003 | Burkus et al. |
| 6,652,533 B2 * | 11/2003 | O'Neil ......................... 606/100 |
| 6,656,190 B2 | 12/2003 | Petit et al. |
| 6,660,038 B2 | 12/2003 | Boyer, II et al. |
| 6,676,703 B2 | 1/2004 | Biscup |
| 6,699,288 B2 | 3/2004 | Moret et al. |
| 6,709,438 B2 | 3/2004 | Dixon et al. |
| 6,712,819 B2 | 3/2004 | Zucherman et al. |
| 6,712,825 B2 | 3/2004 | Aebi et al. |
| 6,719,760 B2 | 4/2004 | Dorchak et al. |
| 6,719,794 B2 | 4/2004 | Gerber et al. |
| 6,743,234 B2 | 6/2004 | Burkus et al. |
| 6,746,454 B2 | 6/2004 | Winterbottom et al. |
| 6,746,484 B1 | 6/2004 | Liu et al. |
| 6,767,367 B1 | 7/2004 | Michelson |
| 6,770,074 B2 | 8/2004 | Michelson |
| 6,805,716 B2 | 10/2004 | Ralph et al. |
| 6,810,994 B2 * | 11/2004 | Trask ............................... 182/3 |
| 6,855,148 B2 | 2/2005 | Foley et al. |
| 6,857,343 B1 | 2/2005 | Easterbrooks et al. |
| 6,896,676 B2 | 5/2005 | Zubok et al. |
| 6,902,566 B2 | 6/2005 | Zucherman et al. |
| 7,396,357 B2 * | 7/2008 | Tornier et al. .................... 606/91 |
| 2001/0016741 A1 | 8/2001 | Burkus et al. |
| 2001/0020170 A1 * | 9/2001 | Zucherman et al. ............ 606/99 |
| 2001/0031967 A1 | 10/2001 | Nicholson et al. |
| 2001/0053914 A1 | 12/2001 | Landry et al. |
| 2002/0010473 A1 | 1/2002 | Lin |
| 2002/0019637 A1 | 2/2002 | Frey et al. |
| 2002/0022887 A1 | 2/2002 | Huene |
| 2002/0055745 A1 | 5/2002 | McKinley et al. |
| 2002/0065560 A1 | 5/2002 | Varga et al. |
| 2002/0068936 A1 | 6/2002 | Burkus et al. |
| 2002/0082695 A1 | 6/2002 | Neumann |
| 2002/0099382 A1 | 7/2002 | Salazar et al. |
| 2002/0099383 A1 | 7/2002 | Salazar et al. |
| 2002/0111632 A1 | 8/2002 | Lechot |
| 2002/0116004 A1 | 8/2002 | McGahan et al. |
| 2002/0143343 A1 | 10/2002 | Castro |
| 2002/0151891 A1 | 10/2002 | Glenn et al. |
| 2002/0161366 A1 | 10/2002 | Robie et al. |
| 2002/0161375 A1 | 10/2002 | Ralph et al. |
| 2002/0165612 A1 | 11/2002 | Gerber et al. |
| 2002/0188295 A1 | 12/2002 | Martz et al. |
| 2003/0032960 A1 | 2/2003 | Dudasik |
| 2003/0060886 A1 | 3/2003 | Van Hoeck et al. |
| 2003/0093082 A1 | 5/2003 | Campbell et al. |
| 2003/0097135 A1 | 5/2003 | Penenberg |
| 2003/0100906 A1 | 5/2003 | Rosa et al. |
| 2003/0100907 A1 | 5/2003 | Rosa et al. |
| 2003/0105466 A1 | 6/2003 | Ralph et al. |
| 2003/0105467 A1 | 6/2003 | Ralph et al. |
| 2003/0109883 A1 | 6/2003 | Matsuzaki et al. |
| 2003/0153916 A1 | 8/2003 | Michelson |
| 2003/0171814 A1 | 9/2003 | Muhanna et al. |
| 2003/0187453 A1 | 10/2003 | Schlapfer et al. |
| 2003/0187454 A1 | 10/2003 | Gill et al. |
| 2003/0191472 A1 | 10/2003 | Michelson |
| 2003/0195520 A1 | 10/2003 | Boyd et al. |
| 2003/0204193 A1 | 10/2003 | Gabriel et al. |
| 2003/0204262 A1 | 10/2003 | Ferguson et al. |
| 2003/0220650 A1 | 11/2003 | Major et al. |
| 2003/0225414 A1 | 12/2003 | Shimp |

| | | |
|---|---|---|
| 2003/0229353 A1 | 12/2003 | Cragg |
| 2003/0229355 A1 | 12/2003 | Keller |
| 2003/0233097 A1 | 12/2003 | Ferree |
| 2003/0233100 A1 | 12/2003 | Santarella et al. |
| 2004/0010261 A1 | 1/2004 | Hoag et al. |
| 2004/0010262 A1 | 1/2004 | Parkinson et al. |
| 2004/0024406 A1 | 2/2004 | Ralph et al. |
| 2004/0024407 A1 | 2/2004 | Ralph et al. |
| 2004/0024408 A1 | 2/2004 | Burkus et al. |
| 2004/0030346 A1 | 2/2004 | Frey et al. |
| 2004/0049202 A1 | 3/2004 | Berger |
| 2004/0073219 A1 | 4/2004 | Skiba et al. |
| 2004/0087947 A1 | 5/2004 | Lim et al. |
| 2004/0093083 A1 | 5/2004 | Branch et al. |
| 2004/0097932 A1 | 5/2004 | Ray et al. |
| 2004/0102790 A1 | 5/2004 | Ralph et al. |
| 2004/0106927 A1 | 6/2004 | Ruffner et al. |
| 2004/0117020 A1 | 6/2004 | Frey et al. |
| 2004/0122442 A1 | 6/2004 | Lewis |
| 2004/0143332 A1 | 7/2004 | Krueger et al. |
| 2004/0147937 A1 | 7/2004 | Dunbar et al. |
| 2004/0153065 A1 | 8/2004 | Lim |
| 2004/0162617 A1 | 8/2004 | Zucherman et al. |
| 2004/0167534 A1 | 8/2004 | Errico et al. |
| 2004/0167535 A1 | 8/2004 | Errico et al. |
| 2004/0167537 A1 | 8/2004 | Errico et al. |
| 2004/0167538 A1 | 8/2004 | Gerber et al. |
| 2004/0176774 A1 | 9/2004 | Zubok et al. |
| 2004/0176780 A1 | 9/2004 | Knopfle et al. |
| 2004/0181233 A1 | 9/2004 | Michelson |
| 2004/0204714 A1 | 10/2004 | Liu et al. |
| 2004/0220567 A1 | 11/2004 | Eisermann et al. |
| 2004/0220581 A1 | 11/2004 | Foley et al. |
| 2004/0220582 A1 | 11/2004 | Keller |
| 2004/0225295 A1 | 11/2004 | Zubok et al. |
| 2004/0230306 A1 | 11/2004 | Hoeck et al. |
| 2004/0236342 A1 | 11/2004 | Ferree et al. |
| 2004/0267275 A1 | 12/2004 | Cournoyer et al. |
| 2004/0267277 A1 | 12/2004 | Zannis et al. |
| 2005/0010213 A1 | 1/2005 | Stad et al. |
| 2005/0010295 A1 | 1/2005 | Michelson |
| 2005/0015094 A1 | 1/2005 | Keller |
| 2005/0015095 A1 | 1/2005 | Keller |
| 2005/0021041 A1 | 1/2005 | Michelson |
| 2005/0021042 A1 | 1/2005 | Marnay et al. |
| 2005/0033305 A1 | 2/2005 | Schultz |
| 2005/0033307 A1 | 2/2005 | Cook et al. |
| 2005/0038431 A1 | 2/2005 | Bartish et al. |
| 2005/0038445 A1 | 2/2005 | Errico et al. |
| 2005/0038517 A1 | 2/2005 | Carrison et al. |
| 2005/0043740 A1 | 2/2005 | Haid et al. |
| 2005/0055031 A1 | 3/2005 | Lim |
| 2005/0072277 A1 | 4/2005 | Knox et al. |
| 2005/0075643 A1 | 4/2005 | Schwab et al. |
| 2005/0085910 A1 * | 4/2005 | Sweeney ................. 623/17.11 |
| 2005/0090824 A1 | 4/2005 | Shluzas et al. |
| 2005/0119665 A1 | 6/2005 | Keller |
| 2005/0131419 A1 | 6/2005 | McCord et al. |
| 2005/0131420 A1 | 6/2005 | Techiera et al. |
| 2005/0131421 A1 | 6/2005 | Anderson et al. |
| 2005/0137602 A1 | 6/2005 | Assell et al. |
| 2005/0143747 A1 | 6/2005 | Zubok et al. |
| 2005/0143749 A1 | 6/2005 | Zalenski et al. |
| 2005/0150335 A1 | 7/2005 | Crane |
| 2005/0154396 A1 | 7/2005 | Foley et al. |
| 2005/0165398 A1 | 7/2005 | Reiley |
| 2005/0165408 A1 | 7/2005 | Puno et al. |
| 2005/0171554 A1 | 8/2005 | Estes et al. |
| 2005/0187558 A1 | 8/2005 | Johnson et al. |
| 2005/0192589 A1 | 9/2005 | Raymond et al. |
| 2005/0203532 A1 | 9/2005 | Ferguson et al. |
| 2005/0203538 A1 | 9/2005 | Lo et al. |
| 2005/0236342 A1 | 10/2005 | Jeong |
| 2006/0074418 A1 * | 4/2006 | Jackson ......................... 606/61 |
| 2006/0129238 A1 * | 6/2006 | Paltzer ..................... 623/17.11 |
| 2007/0093897 A1 * | 4/2007 | Gerbec et al. .............. 623/17.11 |

FOREIGN PATENT DOCUMENTS

| | | |
|---|---|---|
| EP | 1 437 105 | 7/2004 |
| FR | 2615097 | 11/1988 |
| FR | 2736537 | 1/1997 |
| GB | 2307861 | 6/1997 |
| WO | 95/08306 | 3/1995 |
| WO | 95/25487 | 9/1995 |
| WO | WO-9715248 | 5/1997 |

OTHER PUBLICATIONS

Anterior Lumbar Interbody Fusion (ALIF), Product Information, Synthes Spine, 2001.
Peek Titanium, Surgical Technique, The PLIF Solution, Stryker Spine, 2000.
Peek, The High Tech Solution, Stryker Spine, (date not known).
Ray Threaded Fusion Cage Device and Ray TFC Unite Device, Stryker Spine, 2003.
Titanium, Immediate Stability, Stryker Spine, 2003.

* cited by examiner

COLLET-ACTIVATED DISTRACTION WEDGE INSERTER

BACKGROUND OF THE INVENTION

The human spinal column provides support for the body while also protecting the delicate spinal cord and nerves traveling along the spinal column. In general, the spinal column comprises a series of vertebrae stacked on top of each other with an intervertebral disc between each vertebrae. The intervertebral discs advantageously provide cushioning and dampening of compressive forces to the spinal column. For various reasons, including traumatic injury or natural causes, the intervertebral discs may be damaged or otherwise compromised. In such cases, it is known that intervertebral disc replacement devices, such as fusion devices, may be inserted to replace the failing disc or a portion thereof. In order to facilitate placement of such devices, the disc may be removed in whole or in part and the intervertebral disc replacement device inserted between the vertebral bodies. During this procedure, adjacent vertebrae may be distracted by a distraction instrument to assist with the removal process, endplate preparation, or other portions of the procedure.

Present distraction instruments include wedges that may be inserted into the disk area for temporarily supporting the spinal structure. Conventional wedges may be threaded onto an installation tool, which typically comprises an elongated shaft with a handle, the shaft having external threads at its distal end for engagement with internal threads of the wedge. Once inserted, the tool may be rotated and unthreaded from the wedge with the wedge left in place temporarily distracting the adjacent vertebrae. The unthreading of the tool from the wedge distractor is certainly time consuming and may be difficult because of cross-threading. Alternatively, the tool may be left in place while other portions of the overall procedure are undertaken by the surgeon. However, this leaves the tool in the surgeon's line of sight.

Even after tool removal, reattachment leads to more time consumption and cumbersome work. When a wedge is left in place without the tool, and it is desired that the wedge be removed, the surgeon may rethread the tool onto the wedge, and pull the wedge from within the disk bore. It may be difficult, however, for a surgeon to achieve this rethreading because of limited access and visibility. For example, it may be difficult for a surgeon to locate the internally threaded aperture of the wedge with the distal end of the tool. Even when it is located, it is then difficult to thread the tool into the wedge without the tool becoming disengaged from the wedge during the rotation process. There is also the possibility of cross-threading on reattachment.

Accordingly, there remains a need for a tool that can insert a distraction wedge easily and accurately, and can then be reattached quickly and securely to the wedge for wedge removal.

SUMMARY OF THE INVENTION

The present invention overcomes the shortcomings of the prior art by providing, in certain embodiments, a device for inserting and removing a distraction wedge, the device comprising an outer member having a handle and an outer shaft, the outer shaft extending from the handle along a central axis from a proximal end of the outer member to a distal end of the outer member, the handle having a bore, the bore being in-line with the central axis, at least a portion of the bore being internally threaded, the outer shaft having at least one collet formed between a pair of slots extending from the distal end of the outer shaft toward the handle, the at least one collet having a cammed surface on the interior surface thereof. The device also comprises an inner member having a roller and a rod, the rod extending from the roller along a central axis from a proximal end of the inner member to a head formed at a distal end of the inner member, the rod having a threaded portion configured to mate with the internally threaded portion of the handle such that threading of the rod into the handle serves to advance the rod within the outer member toward the distal end of the outer member, whereby the rod is long enough with respect to the outer shaft that the head interferes with the cammed surface of the at least one collet to move the at least one collet outwardly in a radial direction from the central axis of the outer member.

The at least one collet may have a free end at the distal end of the shaft and a fixed end toward the proximal end, the fixed end formed at the proximal limit of the slots.

The at least one collet may include a shoulder between the fixed end and the free end.

The at least one collet may include a shoulder at the fixed end.

The shaft may be comprised of an upper shaft at its proximal end and a lower shaft at its distal end, the upper shaft having a diameter greater than that of the lower shaft.

The device may further comprise a tapered portion between the upper shaft and the lower shaft.

The handle and the shaft may form a T-shaped device.

The roller may be a hand manipulable roller.

The at least one collet may be four collets and the pair of slots may be two of four total slots.

The handle may further comprise a cavity, the roller adapted to at least partially fit within the cavity when threaded in the handle.

In accordance with additional aspects of the present invention, a system for spacing orthopedic bodies is provided where the system comprises at least two wedges, each adapted to be inserted between a first orthopedic body and a second orthopedic body to distract the bodies away from each other, the wedge having an internal cavity; a distraction instrument for engaging with the internal cavity of the wedge, the instrument comprising an outer member and an inner member; the outer member formed from a handle and an outer shaft, the outer shaft extending from the handle along a central axis from a proximal end of the outer member to a distal end of the outer member, the handle having a bore, the bore being in-line with the central axis, at least a portion of the bore being internally threaded, the outer shaft having collets formed between slots which extend from the extreme distal end of the outer shaft toward the handle such that the collets include a free end and a fixed end, the fixed end being at the termination of the slots, the collets having a cammed internal surface; the inner member formed from a roller and a rod, the rod extending from the roller along a central axis from a proximal end of the inner member to a pusher formed at a distal end of the inner member, the rod having a threaded portion configured to mate with the internally threaded portion of the handle such that threading of the rod into the handle by rotating the roller serves to advance the rod within the outer member toward the distal end of the outer member, whereby the rod is long enough with respect to the outer shaft that the pusher interferes with the cammed surface of the collet to deform the collet outwardly in a radial direction from the central axis; wherein the collets are insertable into the internal cavity of the wedge and moved outwardly to secure the wedge to the device.

The collets may include shoulders and the wedge may include aperture extensions into which the shoulders may fit.

The cavity of the wedge may include inside limits, the shoulders adapted to abut the inside limits when the device is fully inserted into the cavity.

The handle and the shaft may form a T-shape.

The handle may include a cavity, at least a portion of the roller adapted to fit within the cavity.

The roller may abut the handle when the collets are deformed outwardly a sufficient distance to secure the wedge to the device.

In accordance with a further aspect of the present invention, a method of distracting orthopedic bodies with a wedge having an internal cavity and an instrument having at least one collet adapted to fit freely within the cavity while in a first position and to frictionally engage the internal cavity after expanding to a second position is disclosed, the method comprising inserting the at least one collet of the instrument into the internal cavity of the wedge while the collet is in the first position; expanding the at least one collet into the second position to frictionally engage the wedge; inserting the wedge between two orthopedic bodies to distract the bodies.

The method may further comprise retracting the at least one collet from the second expanded position back to the first position; removing the instrument from the wedge.

The method may further comprise inserting the at least one collet of the instrument into the internal cavity of the wedge while the collet is in the first position; expanding the at least one collet into the second position to frictionally engage the wedge; removing the wedge from between the two orthopedic bodies.

Within the method, the device may further comprise a roller, and expansion of the at least one collet is achieved by rotation of the roller in a first direction.

BRIEF DESCRIPTION OF THE DRAWINGS

The subject matter regarded as the invention is particularly pointed out and distinctly claimed in the claims. The invention, however, both as to organization and methods of operation, together with features objects, and advantages thereof, may be best understood by reference to the following detailed description when read with the accompanying drawings in which:

DETAILED DESCRIPTION

Figure 1:
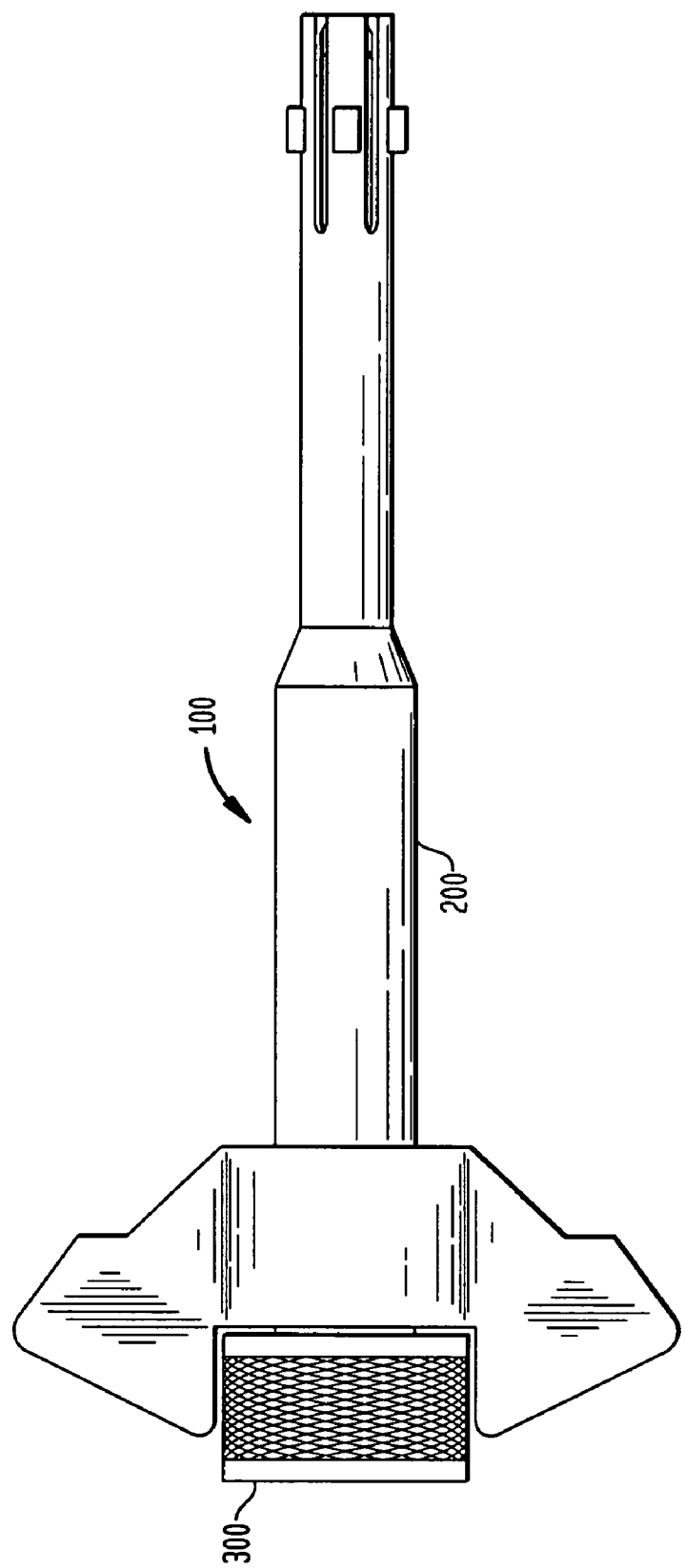
FIG. 1 is a plan view of a fully assembled collet-activated distraction wedge inserter in accordance with certain aspects of the present invention.

In the following are described the preferred embodiments of the collet-activated distraction wedge inserter in accordance with the present invention. In describing the embodiments illustrated in the drawings, specific terminology will be used for the sake of clarity. However, the invention is not intended to be limited to the specific terms so selected, and it is to be understood that each specific term includes all technical equivalents that operate in a similar manner to accomplish a similar purpose. Where like elements have been depicted in multiple embodiments, identical reference numerals have been used in the multiple embodiments for ease of understanding.

As previously stated, the present invention relates to distraction wedge inserters, and more specifically collet-activated distraction wedge inserters. Such inserters may be utilized to capture a distraction wedge at a distal end of the inserter, such that the wedge may be inserted between intervertebral bodies to provide access to the vertebrae for the procedure of, for example, implanting a permanent intervertebral disk replacement device. Together, the inserter and wedge distract the vertebral bodies. The inserter may then be temporarily disassociated with the wedge with the wedge left in place. This provides the surgeon with better access and visibility than he would have with the inserter in place. When it is desired that the wedge be removed from the spinal column, the inserter may then be quickly and positively reassociated with the wedge such that the wedge may be removed. In accordance with the present invention, such association of the inserter and wedge is achieved by frictional relation between radially expanding collets of the inserter and an aperture formed in the wedge, as will be discussed more fully below.

As shown in FIG. 1, a collet-activated distraction wedge inserter 100 may comprise an outer member 200 and an inner member 300, where the inner member is adapted to fit within the outer member.

Figure 2:
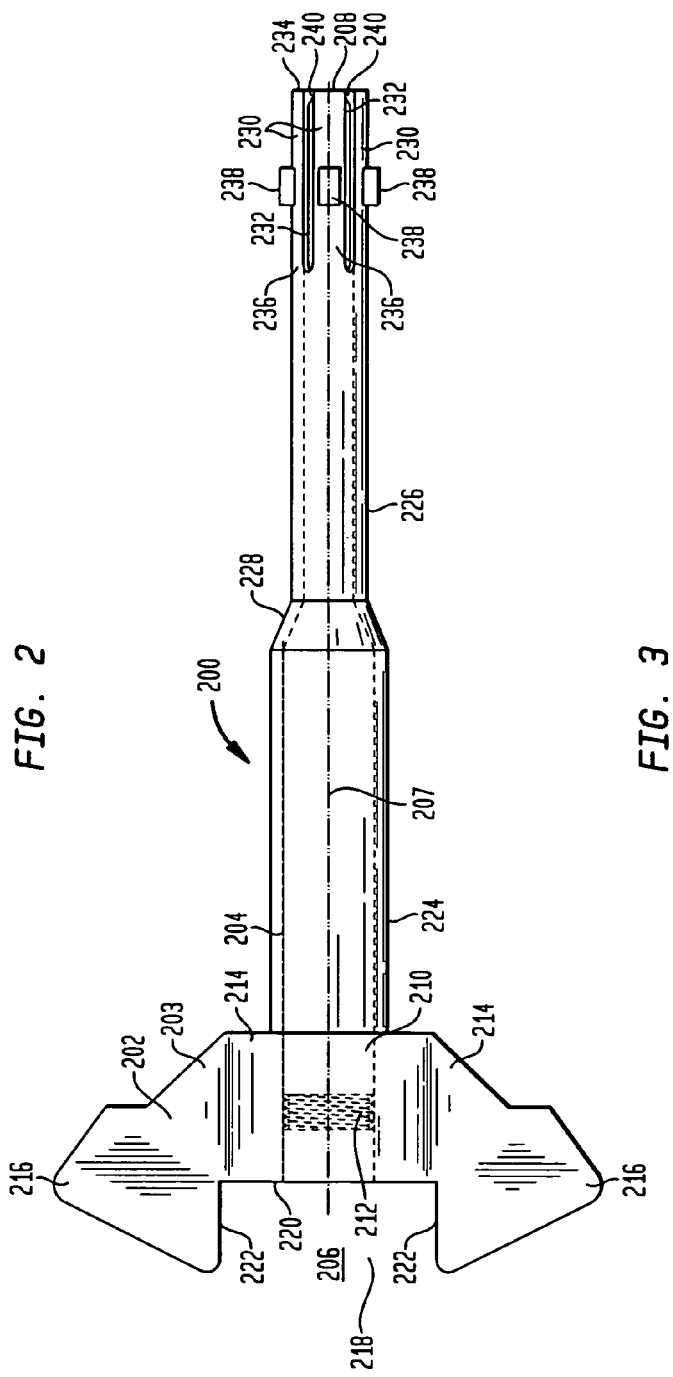
FIG. 2 is a plan view of an outer member forming a portion of the collet-activated distraction wedge inserter of FIG. 1, with certain internal portions shown in phantom for clarity.

FIG. 2 depicts a plan view of the outer member 200 in accordance with a preferred embodiment of the present invention. It is observed in FIG. 2 that the outer member 200 includes a handle 202 and a shaft 204 extending from the handle. The shaft 204, which has a circular cross-section, extends through the handle 202 from a proximal end 206 of the outer member 200 to a distal end 208 along the length of a longitudinal centerline 207. The shaft 204 is hollow such that a bore 210 extends along its entire length from the proximal end 206 to the distal end 208. Within the handle 202, the bore 210 includes a threaded portion 212 which will be discussed in more detail below.

The shaft 204 may be connected to the handle 202 by any conventional biocompatible means, including pressure fit, threading, welding, chemical adhesion, or the like, such that the shaft and handle are virtually inseparable.

The handle 202 is generally formed from a handle base 214, from which the shaft 204 extends, and handle projections 216 extending outwardly from the handle base 214 to form a cavity 218 at the proximal end 206 of the outer member 200. It will be appreciated that in the preferred embodiment the cavity is formed from a bearing surface 220 at the handle base 214 and a pair of upstanding walls 222, formed by the handle projections 216 respectively. The handle 202 includes a flat front face 203 and a flat rear face (not shown), and forms a generally T-shape with the shaft 204. Preferably, the device 100 and particularly the associated handle 202 are ergonomically configured to permit ease and comfort in use. The device 100 is also configured to permit one-handed use by grasping of the handle 202, if so desired.

The shaft 204 is comprised of an upper shaft 224 and an adjacent lower shaft 226, the upper shaft being closest to the handle 202. It will be appreciated that the upper shaft 224 is formed to a greater diameter than the lower shaft 226 such that there resides a tapered portion 228 therebetween. At the distal end 208 of the lower shaft 226, there is formed at least one collet 230. In the preferred embodiment shown in FIG. 2, there are four such collets 230, with the rear-most collet being hidden from view in FIG. 2. The collets 230 are created by slots 232 formed in the hollow lower shaft 226 from the distal end 208 and extending toward the proximal end 206 such that each collet 230 includes a distal end 234 at the extreme distal end 208 of the lower shaft 226 and a proximal end 236 at a point toward the tapered portion 228 where the slot 232 ends. Each collet 230 is therefore cantilevered from the remainder of the lower shaft 226 at its respective proximal end 236.

The collets 230 may each include a shoulder 238 extending outwardly from the collet's outer surface. A shoulder can be provided on less than each collet, but there are preferably at least two, and in the preferred embodiment one for each collet. Preferably, the shoulder 238 has an extreme outer diameter approximately equal to the diameter of the upper shaft 224, which, as noted, is greater than the diameter of the lower shaft 226. Of course, the shoulders on the collets may be replaced with one shoulder or a number of shoulders on the shaft 226 above the collets. Such a shoulder might be a single continuous annular shoulder.

The shoulders 238 may be configured on the collet 230 at the approximate mid-point between the distal end 234 and the proximal end 236. Alternatively, the shoulders 238 may be configured at the proximal end 236 of each collet 230. It will also be appreciated that the shoulders 238 may be located on the lower shaft 226 beyond the limits of the slots 232, or closer toward the distal end 208. The number of shoulders 238 may be less than that of the total number of collets 230, if so desired. Alternatively, the collets 230 may not include shoulders 238.

At the distal end 208 of each collet 230, the collet's inner surface forms a cammed surface 240. It will be appreciated that the cammed surface 240 is in essence an angled projection having an inner diameter less than that of the inner diameter of the lower shaft 226. The function of the cammed surface 240 will be discussed more fully below, but it will be appreciated that a rod that may freely fit within the lower shaft 226 may be cammed against the cammed surface 240 to force open the distal end 234 of each collet and spread apart same radially to create an outer diameter at the distal end 234 which is greater than the outer diameter of the remainder of the lower shaft 226. This expansion may be utilized to secure a wedge.

Figure 3:
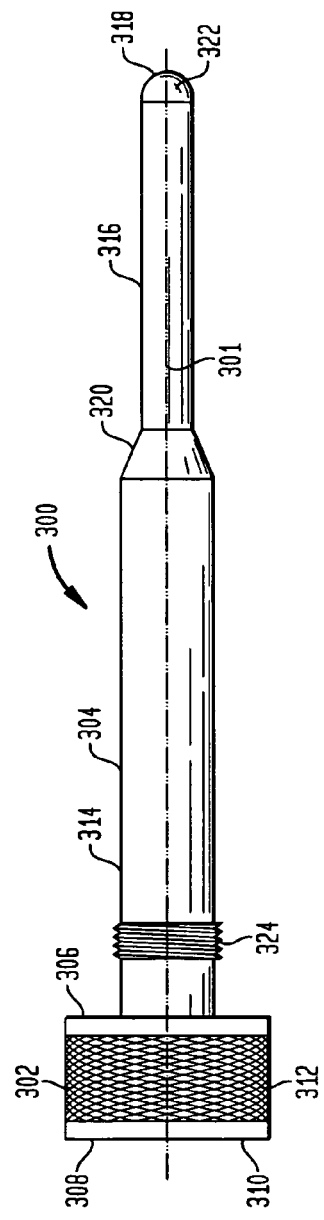
FIG. 3 is a plan view of an inner member forming a portion of the collet-activated distraction wedge inserter of FIG. 1.

As shown in FIG. 3, the inner member 300 may comprise a roller 302 with a rod 304 extending along a central axis 301 therefrom. The roller 302 may be formed between a base 306 at intersection of the roller 302 and the rod 304 to an upper limit 308 at a proximal end 310 of the inner member 300. The roller 302 may include a knurled portion 312 between the upper limit 308 and the base 306, the knurled portion 312 being utilized for rotational manipulation by the surgeon.

The rod 304 may comprise an upper rod 314 positioned toward the proximal end 310 of the inner member 300 and a lower rod 316 positioned toward the distal end 318 of the inner member 300. The upper rod 314 has an outside diameter greater than that of the lower rod 316, such that a tapered portion 320 lies therebetween. At the extreme distal end 318 of lower rod 316, the lower rod 316 culminates with a shaped head, such as the convex head 322 shown in FIG. 3. As will be discussed, the convex head 322 is utilized to spread apart the collets 230 of the outer member 200 by camming against the cammed surface 240 of each collet. It will therefore be appreciated that other geometric shaped heads, such as cone shaped or pyramid shaped heads, may also be utilized suitably for this purpose.

Figure 4:
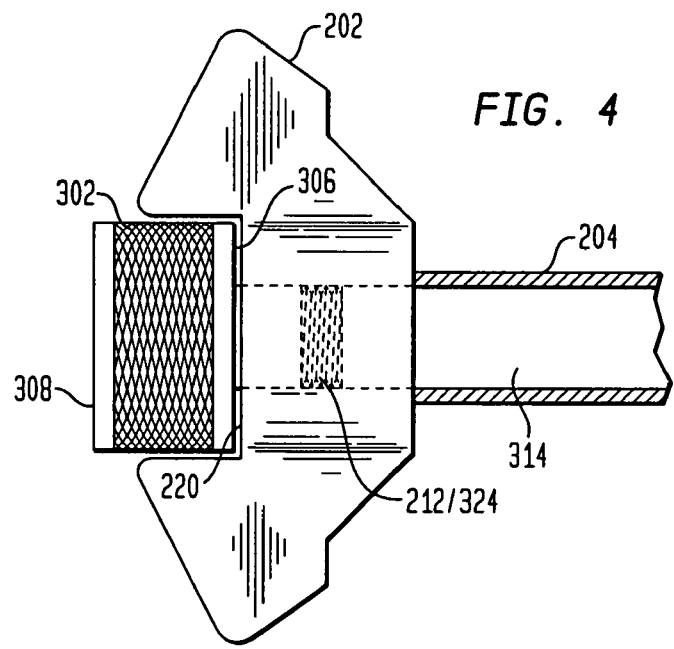
FIG. 4 is a partially cut-away plan view of the fully assembled collet-activated distraction wedge inserter of FIG. 1, with certain internal portions shown in phantom for clarity.

The upper rod 314 also includes a threaded portion 324 adjacent to the roller 302. The inner member 300 is adapted to fit within the outer member 200 such that the threaded portion 324 of the upper rod 314 may thread within the threaded portion 212 of the handle 202. This relationship is shown in FIG. 4. It will be appreciated that as the inner member 300 is threaded into the outer member 200, the convex head 322 moves closer to the cammed surface 240 of each collet 230. When the roller 302 is fully threaded into the handle 202, such that the base 306 of the roller contacts the bearing surface 220 of the cavity 218, the convex head 322 will be fully engaged with the cammed surfaces 240 to spread the collets 230 apart. At such time, the upper limit 308 of the roller 302 may be used as an impact surface against which a mallet may be struck when inserting the wedge to help drive the wedge in place. The force of the mallet will therefore be transferred from the roller 302 to the bearing surface 220 of the handle 202, and not to any of the threaded portions 212, 324.

Figure 5:
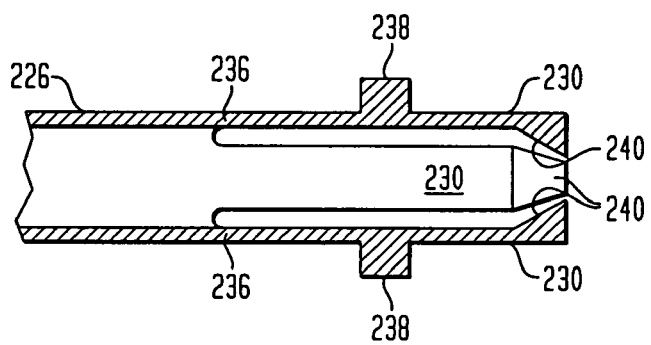
FIG. 5 is a cross-sectional view of the distal end of the outer member shown in FIG. 2.

FIG. 5 depicts a cross-section of the distal end 208 of lower shaft 226 with the front-most collet 230 removed for clarity. In this view, the cammed surfaces 240 can be seen more clearly than in previous figures.

Figure 6:
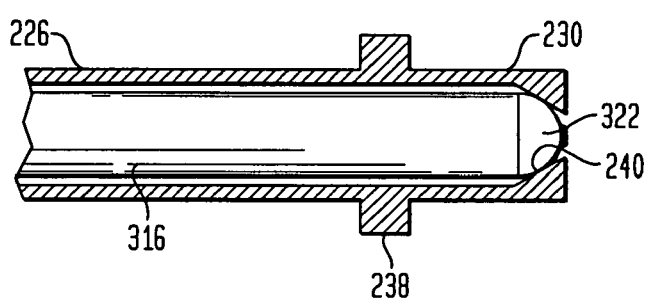
FIG. 6 is a cross-sectional view of the distal end of the outer member shown in FIG. 2 with the inner member shown in FIG. 3 at a first position.
Figure 7:
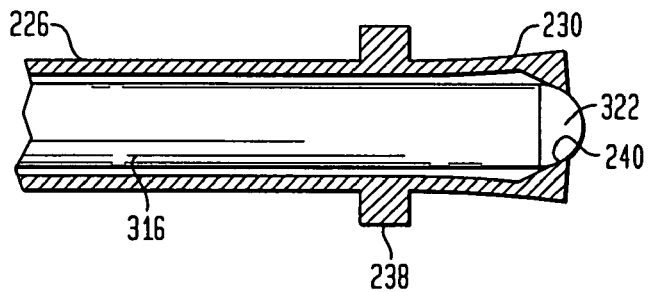
FIG. 7 is a cross-sectional view of the distal end of the outer member shown in FIG. 2 with the inner member shown in FIG. 3 at a second position.

FIG. 6 also depicts a cross-section of the distal end 208 of lower shaft 226 with the front-most collet 230 removed for clarity, but with the lower rod 316 being inserted into the lower shaft 226. In the view shown in FIG. 6, the convex head 322 is adjacent to the cammed surface 240, but has not yet made significant contact as it moves from left to right. As the lower rod 316 is advanced by threading of the threaded portion 324 of the upper rod 314 within the threaded portion 212 of the handle 202, the convex head 322 moves linearly toward the extreme distal end 208 of the lower shaft 226. This movement causes the convex head 322 to contact the cammed surfaces 240 to spread the cammed surfaces apart so as to expand the collets 230 radially outward at their respective distal ends 234 from fixed positions at the proximal ends 236. This relationship opens the distal end 208 of the lower shaft such that the outside diameter at the distal end is greater than that of the remainder of the lower shaft 226. In use, this action spreads the collets 230 to frictionally engage the interior of a cavity, particularly the cavity of a distraction wedge, as will be discussed.

Figure 8:
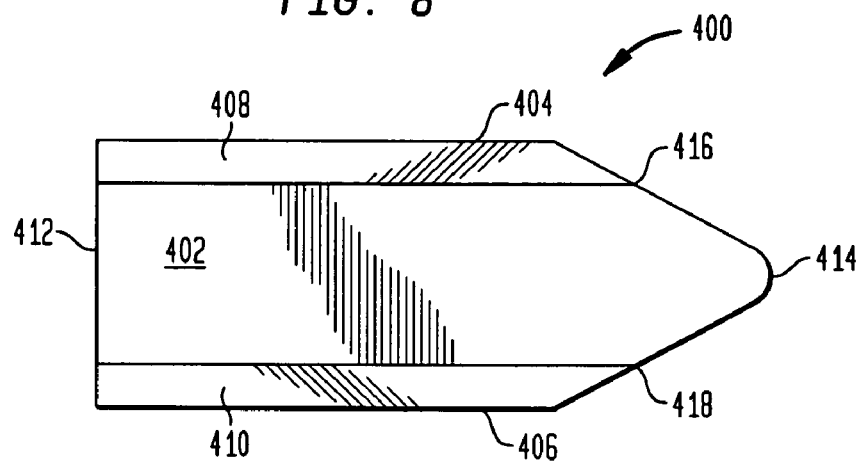
FIG. 8 is a side view of a distraction wedge that may be utilized with the collet-activated distraction wedge inserter of FIG. 1.

FIG. 8 depicts a distraction wedge 400 suitable for use with the collet-activated distraction wedge inserter 100 described herein. As with conventional distraction wedges, distraction wedge 400 may include a side portion 402 tapering to an upper limit 404 and a lower limit 406 with an upper taper 408 and a lower taper 410. The distraction wedge 400 may extend between a back 412 and a tip 414, the tip being formed by an upper angled portion 416 extending from the upper limit 404 to the tip 414 and a lower angled portion 418 extending from the lower limit 408 to the tip 414.

Figure 9:
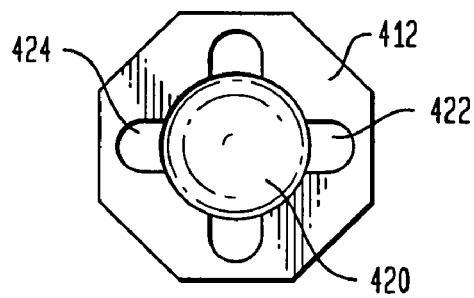
FIG. 9 is a rear view of the distraction wedge of FIG. 8.
Figure 10:
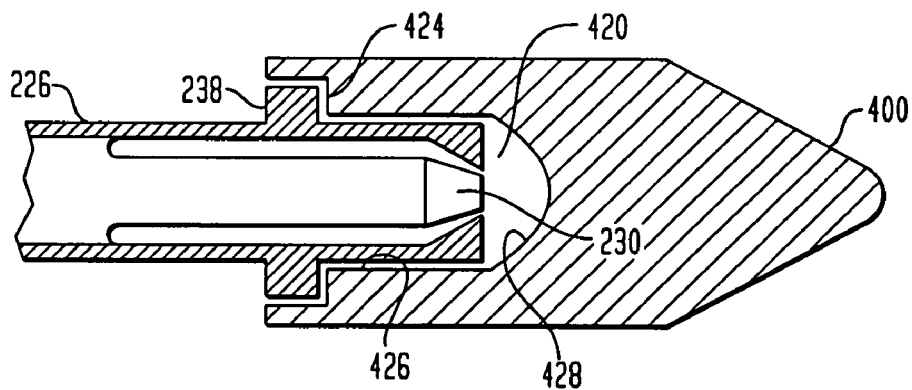
FIG. 10 is a partial cross-sectional view of the collet-activated distraction wedge inserter of FIG. 1 partially engaged with the distraction wedge of FIG. 8.

As shown in FIG. 9, the back 412 may include an aperture 420. The aperture 420 is preferably round and with a diameter slightly larger than the outer diameter of the lower shaft 226, such that the lower shaft may fit within the aperture. The aperture 420 may also include aperture extensions 422 extending from the aperture 420 to permit the shoulders 238 to also fit within the distraction wedge 400. It will be appreciated that the shoulders 238 may abut against the inside limit 424 of the aperture extensions 422 to limit the distance in which the lower shaft 226 may enter the aperture 420. This relationship is best shown in FIG. 10, where the lower shaft 226 has been inserted into the aperture 420 such that the shoulders 238 abut the inside limit 424. Once the lower shaft 226 is positioned as shown in FIG. 10, it will be appreciated that the convex head 322 of the lower rod 316 may be advanced toward the cammed surfaces 240 of the collets 230 to open the collets such that a frictional force is created between the collets and the interior walls 426 of the aperture 420. This force serves to hold the distraction wedge 400 in fixed relation with the collet-activated distraction wedge inserter 100.

The distraction wedge 400 may then be inserted into the spinal cavity of a patient during a surgical procedure to temporarily distract adjacent vertebrae. Once properly inserted, the roller 302 may be rotated in a direction opposite to the rotation required to advance the convex head 322, such that the convex head is retracted into the lower shaft whereby the collets 230 may rebound back to their natural positions with an outside diameter approximately equal to that of the remainder of the lower shaft 226 and removed from the distraction wedge 400.

It will be particularly appreciated that removal of the distraction wedge 400 is made much easier by use of the present invention over prior art techniques. As discussed previously, prior art techniques typically included threading a rod into a distraction wedge, which may be difficult during surgical procedures as the rod often slips off the wedge before threading may begin.

In the present device, the distal end 208 of the device is simply inserted into the aperture 420 of the distraction wedge 400. Because the distal end 208 of the collet-activated distraction wedge inserter 100 may be fully inserted without any threading, it is very easy to instantly fully seat the distal end 208 within the aperture 420. In prior art embodiments, although the distal end of the conventional inserter may be abutted against the aperture of a wedge, the distal end cannot be fully seated without rotating the inserter to fully thread the connection. Surgeons often find that the conventional inserter becomes disassociated with the wedge when such threading is attempted, as the distal end slips off of its engagement with the aperture because the distal end penetrates the aperture only slightly before threading begins.

The surgeon utilizing a collet-activated distraction wedge inserter of the present invention easily ensures that the distal end 208 is fully inserted by simply pushing the distal end 208 into the aperture of the wedge until the shoulders 238 engage the inside limit 424. At such point, the surgeon may rotate the roller 302 to advance the convex head 322 of the lower rod 316 against the cammed surface 240 of the collets 230 to spread the collets apart. In embodiments where shoulders are not provided, the surgeon may insert the distal end 208 of the collet-activated distraction wedge inserter 200 until the distal end abuts the rear wall 428 of the aperture 420.

Preferably, the collet-activated distraction wedge inserter 100 is configured such that the collets 230 are spread apart the optimal distance to create the requisite friction within the aperture 420 at the moment that the base 306 of the roller 302 abuts the bearing surface 220 of the handle 202. At this point, the surgeon may withdraw the collet-activated distraction wedge inserter 100 from within the body along with the distraction wedge 400 due to the frictional relation between the two members.

To enhance the frictional forces created by the radially expanding collets 230, the abutting surfaces of the collets 230 and the aperture 420 of the wedge 400 may be textured. It is preferred that such texturing be suitable for cleaning between uses of the collet-activated distraction wedge inserter 100.

As with many medical devices, the components comprising the collet-activated distraction wedge inserter 100 may be formed from various biocompatible plastics or metal alloys. Particularly suitable alloys are stainless steel or titanium. Further, it will be appreciated that the inner member 300 may easily be withdrawn from the outer member 200 by completely unthreading the threaded portion 324 of the rod 304 from the threaded portion 212 of the handle 202 and withdrawing the inner member 300 from the outer member 200 such that the components may be cleaned and sterilized.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A device for inserting and removing a distraction wedge, said device comprising:
   an outer member having a handle and an outer shaft, said outer shaft extending from said handle along a central axis from a proximal end of said outer member to a distal end of said outer member, said handle having a bore, the bore being in-line with said central axis, at least a portion of said bore being internally threaded, said outer shaft having at least one collet formed between a pair of slots extending from said distal end of said outer shaft toward said handle, said at least one collet having a cammed surface on an interior surface thereof and a shoulder extending from an outer surface thereof, said at least one collet further including a free end at said distal end of said shaft and a fixed end toward said proximal end of said shaft, said fixed end formed at a proximal limit of said slots, wherein the shoulder is located proximal of the free end along the central axis, wherein said shoulder extends further from the central axis than any other portion of the outer surface of the collet;
   an inner member having a roller and a rod, said rod extending from said roller along a central axis from a proximal end of said inner member to a head formed at a distal end of said inner member, the roller fitting at least partially within said handle, said rod having a threaded portion configured to mate with said internally threaded portion of said handle such that threading of said rod into said handle serves to advance said rod within said outer member toward the distal end of said outer member, whereby said rod is long enough with respect to said outer shaft that said head interferes with said cammed surface of said at least one collet to bend said at least one collet outwardly in a radial direction from said central axis of said outer member.

2. The device of claim 1, wherein said outer shaft is comprised of an upper shaft at its proximal end and a lower shaft at its distal end, said upper shaft having a diameter greater than that of said lower shaft.

3. The device of claim 2, further comprising a tapered portion between said upper shaft and said lower shaft.

4. The device of claim 1, wherein said handle and said outer shaft form a T-shaped device.

5. The device of claim 1, wherein said roller is a hand manipulable roller.

6. The device of claim 1, wherein said at least one collet is four collets, and said pair of slots are two of four total slots.

7. The device of claim 1, wherein said handle further comprises a cavity, said roller adapted to at least partially fit within said cavity when threaded in said handle.

8. A system for spacing orthopedic bodies, said system comprising:
a wedge adapted to be inserted between a first orthopedic body and a second orthopedic body to distract the bodies away from each other, the wedge having an internal cavity;
a distraction instrument for engaging with said internal cavity of said wedge, said instrument comprising an outer member and an inner member;
said outer member formed from a handle and an outer shaft, said outer shaft extending from said handle along a central axis from a proximal end of said outer member to a distal end of said outer member, said handle having a bore, said bore being in-line with said central axis, at least a portion of said bore being internally threaded, said outer shaft having collets formed between slots which extend from the extreme distal end of the outer shaft toward said handle such that said collets include a free end and a fixed end, said fixed end being at the termination of said slots, said collets having a cammed internal surface and a shoulder extending from an outer surface thereof, wherein the shoulder is located proximal of the free end along the central axis, wherein said shoulder extends further from a central axis than any other portion of the outer surface of the collet;
said inner member formed from a roller and a rod, said rod extending from said roller along a central axis from a proximal end of said inner member to a pusher formed at a distal end of said inner member, said rod having a threaded portion configured to mate with said internally threaded portion of said handle such that threading of said rod into said handle by rotating said roller serves to advance said rod within said outer member toward said distal end of said outer member, the roller fitting at least partially within said handle, whereby said rod is long enough with respect to said outer shaft that said pusher interferes with said cammed surface of said collet to deform said collet outwardly in a radial direction from said central axis;
wherein said collets are insertable into said internal cavity of said wedge and moved outwardly to secure said wedge to said instrument.

9. The system of claim 8, wherein said wedge includes aperture extensions into which said shoulders may fit.

10. The system of claim 9, wherein said cavity of said wedge includes inside limits, said shoulders adapted to abut said inside limits when said device is fully inserted into said cavity.

11. The system of claim 8, wherein said handle and said outer shaft form a T-shape.

12. The system of claim 8, wherein said handle includes a cavity, at least a portion of said roller adapted to fit within said cavity.

13. The system of claim 8, wherein said roller abuts said handle when said collets are deformed outwardly a sufficient distance to secure said wedge to said device.

14. A method of distracting orthopedic bodies with a wedge having an internal cavity and an instrument having at least one collet formed from an outer shaft of the instrument, the at least one collet having a shoulder that extends from an outer surface of the at least one collet and is located proximal of a distal end of the outer shaft, wherein said shoulder extends further from a central axis of the outer member than any other portion of the outer surface of the at least one collet, the at least one collet adapted to fit freely within the cavity while in a first position and to frictionally engage the internal cavity after expanding to a second position achieved when an inner shaft of the instrument is threaded and advanced within the outer shaft by virtue of a roller located at least partially within a handle associated with the outer shaft, said method comprising:
inserting the at least one collet of the instrument into the internal cavity of the wedge while the collet is in the first position;
abutting said shoulders with inside limits of said cavity of said wedge;
expanding the at least one collet into the second position by threading the inner shaft within the outer shaft to frictionally engage the wedge;
inserting the wedge between two orthopedic bodies to distract the bodies.

15. The method of claim 14, further comprising:
retracting the at least one collet from the second expanded position back to the first position;
removing the instrument from the wedge.

16. The method of claim 15, further comprising:
inserting the at least one collet of the instrument into the internal cavity of the wedge while the collet is in the first position;
expanding the at least one collet into the second position to frictionally engage the wedge;
removing the wedge from between the two orthopedic bodies.

17. The method of claim 14, wherein expansion of the at least one collet is achieved by rotation of the roller in a first direction.

18. The device of claim 1, wherein said roller is disposed at least partially within a proximal end of said handle when the device is in a fully assembled position in which the threaded portion of the rod is mated with the internally threaded portion of the handle.

19. The system of claim 8, wherein said roller is disposed at least partially within the proximal end of said handle when the instrument is in a fully assembled position in which the threaded portion of the rod is mated with the internally threaded portion of the handle.

20. The method of claim 14, wherein said roller is located at least partially within a proximal end of said handle, opposite said at least one collet formed at a distal end of said instrument, when the device is in the second position.

* * * * *